United States Patent [19]

Sohda et al.

[11] Patent Number: 5,441,971
[45] Date of Patent: Aug. 15, 1995

[54] THIAZOLIDINEDIONE DERIVATIVES, PRODUCTION AND USE THEREOF

[75] Inventors: Takashi Sohda; Hitoshi Ikeda, both of Osaka, Japan; John C. Greenfield, Richland, Mich.; Jerry R. Colca, Texas Township, Mich.; Edgar N. Petzold, Plainwell, Mich.

[73] Assignees: The Upjohn Company, Kalamazoo, Mich.; Takeda Chemical Industries, Ltd., Osaka, Japan

[21] Appl. No.: 137,135

[22] PCT Filed: Apr. 6, 1992

[86] PCT. No.: PCT/US92/02566

§ 371 Date: Oct. 12, 1993

§ 102(e) Date: Oct. 12, 1993

[87] PCT Pub. No.: WO92/18501

PCT Pub. Date: Oct. 29, 1992

[30] Foreign Application Priority Data

Apr. 11, 1991 [JP] Japan .................... 3-078836

[51] Int. Cl.[6] ..................... A61K 31/44; C07D 417/12
[52] U.S. Cl. ........................ 514/342; 546/280
[58] Field of Search .................. 546/280; 514/342

[56] References Cited

U.S. PATENT DOCUMENTS

| 4,444,779 | 4/1984 | Kawamatsu et al. | 424/263 |
| 4,582,839 | 4/1986 | Meguro | 514/342 |
| 4,687,777 | 8/1987 | Meguro et al. | 514/342 |
| 5,183,823 | 2/1993 | Sohda et al. | 514/358 |

FOREIGN PATENT DOCUMENTS

| 0008203 | 2/1980 | European Pat. Off. ... C07D 277/34 |
| 0193256 | 9/1986 | European Pat. Off. ... C07D 417/12 |

OTHER PUBLICATIONS

Sohda et al. CA113(3):23750k, 1990.
Meguro CA 104(21):186401a, 1985.
T. Sohda, et al., Chemical and Pharmaceutical Bulletin, "Studies on Antidiabetic Agents, II. Synthesis of 5-[4-(-1-Methylcyclohexylmethoxy)-Benzyl]Thiazolidine-2,-4-Dione (ADD-3878) and its Derivatives", pp. 3580-3600, vol. 30, No. 10, (Oct. 1982).

*Primary Examiner*—Jane Fan
*Attorney, Agent, or Firm*—Lawrence T. Welch

[57] ABSTRACT

A thiazolidinedione compound of the formula

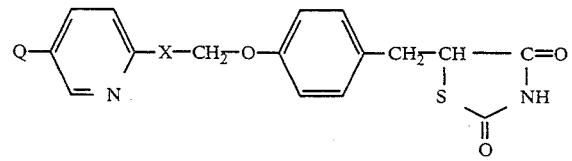

wherein X,Q are as defined in the specification. The compounds are used for treating diabetes.

21 Claims, No Drawings

THIAZOLIDINEDIONE DERIVATIVES, PRODUCTION AND USE THEREOF

This is the national phase application (35 USC 371) of PCT/U.S. Pat. No. 92/02566 filed Apr. 6, 1992.

FIELD OF THE INVENTION

The present invention relates to novel thiazolidinedione derivatives having hypoglycemic and hypolipidemic activities, the production thereof and a pharmaceutical composition for treating diabetes containing them.

BACKGROUND OF THE INVENTION

Various biguanide compounds and sulfonylurea compounds have been used as agents for treating diabetes. However, at present, biguanide compounds are scarcely used because they cause lactic acidosis. Although sulfonylurea compounds have strong hypoglycemic activity, they often cause serious hypoglycemia and they must be used with caution.

OBJECTS OF THE INVENTION

The present inventors have intensively studied to find out compounds having hypoglycemic activity without the above drawbacks. As a result, it has been found novel thiazolidinedione derivatives having excellent hypoglycemic and hypolipidemic activities. Thus, the present invention have been completed.

The main object of the present invention is to provide novel compounds having no above drawbacks of conventional biguanide compounds and sulfonylurea compounds.

This object as well as other objects and advantages of the present invention will become apparent to those skilled in the art from the following description.

SUMMARY OF THE INVENTION

According to the present invention, there is provided a thiazolidinedione derivative of the general formula (I):

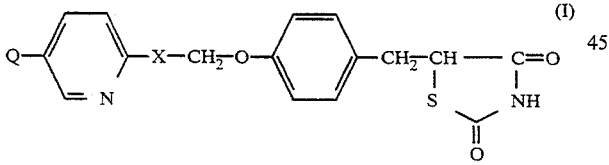

wherein X is —$CH_2$— or —CO—, Q is $CH_3CO$—, $CH_3CH(OR)$— or —$CH_2COOH$, when X is —$CH_2$—, wherein R is a hydrogen atom or an acyl group, or Q is $CH_3CH_2$—, when X is —CO—, a pharmaceutically acceptable salt thereof, or a pure stereoisomeric form thereof.

The present invention also provide a pharmaceutical composition;for treating diabetes comprising as an effective component the thiazolidinedione derivative of the general formula (I), a pharmacologically acceptable salt thereof or a pure stereoisomeric form thereof.

DETAILED DESCRIPTION OF THE INVENTION

Examples of the acyl group represented by R in the general formula (I) include formyl, alkylcarbonyl having 2 to 6 carbon atoms (e.g., acetyl, propionyl, isobutyryl, pentanoyl, isopentanoyl, hexanoyl, etc.), aralkylcarbonyl having 8 to 9 carbon atoms (e.g., phenylacetyl, phenylpropionyl, etc.), arylcarbonyl having 7 to 8 carbon atoms (e.g., benzoyl, p-toluoyl, etc.) and the like. The aralkylcarbonyl and arylcarbonyl may have one or more substituents such as halogen (fluorine, chlorine, bromine, etc.), lower alkoxy having 1 to 4 carbon atoms (methoxy, ethoxy, etc.), trifluoromethyl and the like.

The thiazolidinedione derivative of the general formula (I) (hereinafter referred to as the compound (I)) possesses an acidic nitrogen atom in the thiazolidine ring and a basic nitrogen atom in the pyridine ring. Therefore, the compound (I) of the present invention can exist as both its acidic and basic salts. Examples of the acidic salt include salts with inorganic acids such as hydrochloric acid, hydrobromic acid, sulfuric acid, phosphoric acid and the like, and salts with organic acids such as methanesulfonic acid, toluenesulfonic acid, oxalic acid, malonic acid, maleic acid, fumaric acid, succinic acid, tartaric acid, malic acid and the like. Examples of the basic salt include pharmacologically acceptable salts such as sodium salt, potassium salt, aluminium salt, magnesium salt, calcium salt and the like.

Specific examples of the compound (I) are as follows:
5-[4-[2-(5-acetyl-2-pyridyl)ethoxy]benzyl]-2,4-thiazolidinedione;
5-[4-[2-[5-(1-hydroxyethyl)-2-pyridyl]ethoxy]benzyl]-2,4-thiazolidinedione;
5-[4-[2-[5-(1-acetoxyethyl)-2-pyridyl]ethoxy]benzyl]-2,4-thiazolidinedione;
5-[4-[2-[5-(1-propionyloxyethyl)-2-pyridyl]ethoxy]benzyl]-2,4-thiazolidinedione;
5-[4-[2-[5-(1-butyryloxyethyl)-2-pyridyl]ethoxy]benzyl]-2,4-thiazolidinedione;
5-[4-[2-[5-(1-isobutyryloxyethyl)-2-pyridyl]ethoxy]benzyl]-2,4-thiazolidinedione;
5-[4-[2-[5-(1-valeryloxyethyl)-2-pyridyl]ethoxy]benzyl]-2,4-thiazolidinedione;
5-[4-[2-[5-(1-isovaleryloxyethyl)-2-pyridyl]ethoxy]benzyl]-2,4-thiazolidinedione;
5-[4-[2-[5-(1-pivaloyloxyethyl)-2-pyridyl]ethoxy]benzyl]-2,4-thiazolidinedione;
5-[4-[2-[5-(1-benzoyloxyethyl)-2-pyridyl]ethoxy]benzyl]-2,4-thiazolidinedione;
5-[4-[2-(5-carboxymethyl-2-pyridyl)ethoxy]benzyl]-2,4-thiazolidinedione; and
5-[4-[2-(5-ethyl-2-pyridyl)-2-oxoethoxy]benzyl]-2,4-thiazolidinedione.

The compound (I), the pharmacologically acceptable salt thereof, or the pure stereoisomeric form thereof has hypoglycemic and hypolipidemic activities. Further, the compound (I), the pharmacologically acceptable salt thereof or the pure stereoisomeric form thereof has low toxicity. For example, even when the compound obtained in Example 1 or 2 hereinafter was orally administered to mice in a dose of 300 mg/kg, no lethal case was observed. Therefore, the compound (I), its pharmacologically acceptable salt or pure stereoisomeric form can be used for treatment of diabetes of mammals including man as it is or by combining with a known pharmacologically acceptable carrier, excipient, filler and the like.

Normally, the compound (I), its pharmacologically acceptable salt, stereoisomeric form can be administered orally in the form of, for example, tablets, capsules including soft capsules and micro capsules, powders, granules or the like. If necessary, it can also be administered parenterally in the form of injectable solutions, suppositories, pellets or the like. In the case of oral administration, preferably, it is administered one to three times a day in a daily dose of 0.05 to 10 mg/kg.

The compound (I) and its salt of the present invention can be produced as follows.

(1) Production of the compound (I) wherein X is

—CH$_2$— and Q is CH$_3$CH(OH)—

This compound (I-1) can be produced according to the Scheme 1.

Then, the reaction can be carried out in the presence of a deacidification agent such as sodium acetate, potassium acetate or the like to trap the hydrogen bromide. The deacidification agent is normally used 1 to 1.5 mol per 1 mol of the compound (II). The compound (III) is produced by this reaction. The compound (III) can optionally be isolated, but it can be used without isolation in the next acid hydrolysis step.

Hydrolysis of the compound (III) is normally carried out in a suitable solvent in the presence of water and a mineral acid. Examples of the solvent include the solvents used in the reaction of the compound (II) with

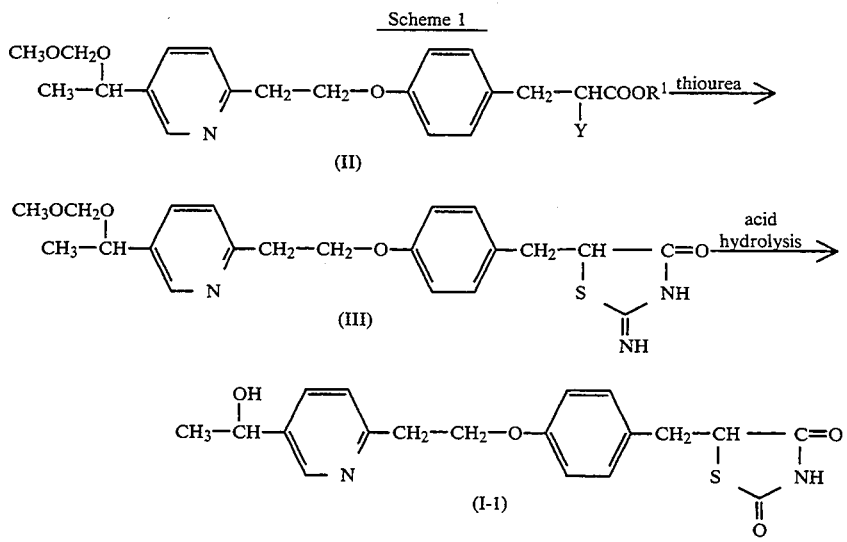

wherein R$^1$ is a hydrogen atom or a lower alkyl group, and Y is a leaving group.

Examples of the lower alkyl group represented by R$^1$ include those having 1 to 4 carbon atoms such as methyl, ethyl, propyl, isopropyl, butyl and the like. In particular, lower alkyl groups having 1 to 3 carbon atoms are preferred. Examples of the leaving group represented by Y include halogen atoms (e.g., chlorine, bromine, iodine), and the like.

The reaction of the compound (II) with thiourea is normally carried out in a solvent such as alcohols (e.g., methanol, ethanol, propanol, 2-propanol, butanol, isobutanol, 2-methoxyethanol or the like), dimethyl sulfoxide, sulfolane or the like. The reaction temperature is normally 20° to 180° C., preferably 50° to 150° C. The amount of thiourea to be used is 1 to 2 mol per 1 mol of the compound (II). In this reaction, hydrogen bromide is generated as a by-product as the reaction proceeds.

thiourea. Examples of the mineral acid include hydrochloric acid, hydrobromic acid, sulfuric acid and the like. The amount of the mineral acid to be used is 0.1 to 20 mol, preferably 0.2 to 10 mol per 1 mol of the compound (III). The water is normally added in large excess. This reaction is normally carried out under warming or heating. The reaction temperature is normally 60° to 150° C. The heating time is normally several hours to twenty and several hours.

(2) Production of the compound (I) wherein X is

—CH$_2$— and Q is CH$_3$CO—

This compound (I-2) can be produced by according to the Scheme 2.

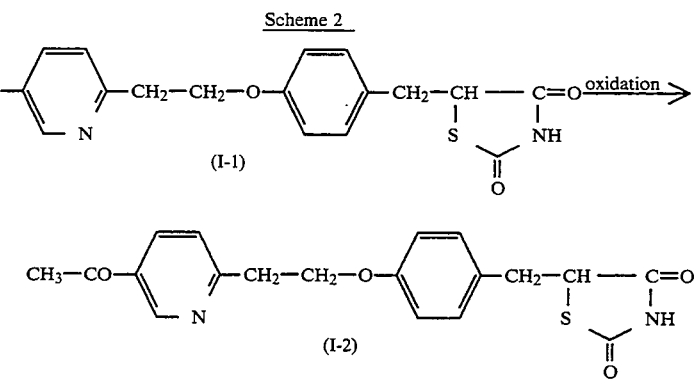

The oxidation can be carried out according to a known method. Examples thereof include oxidation with manganese dioxide, oxidation with chromic acid (e.g., chromium (IV) oxide-pyridine complex), oxidation with dimethyl sulfoxide and the like [see Shin Jikken Kagaku Koza, Vol. 15 (I-1), (I-2), edited by Japan Chemical Society, Maruzen Shuppan, 1976].

For example, in the case of the oxidation with dimethyl sulfoxide, the oxidation is normally carried out in an inert solvent such as chloroform, dichloromethane, benzene, toluene or the like. Dimethyl sulfoxide may be used as the solvent. The oxidation is carried out in the presence of an electrophilic reagent such as acetic anhydride, phosphoric anhydride, dicyclocarbodiimide, chlorine or the like. The reaction is normally carried out at about $-100°$ to $+60°$ C. The reaction time is about 0.5 to 50 hours.

(3) Production of the compound (I) wherein X is $-CH_2-$ and Q is $CH_3CH(OR)-$ and R is other than a hydrogen atom This compound (I-3) can be produced according to the Scheme 3.

lides derived from aliphatic, aryl aliphatic and aromatic carboxylic acids. Examples of the aliphatic carboxylic acid include those having 2 to 6 carbon atoms such as acetic acid, propionic acid, butyric acid, isobutyric acid, valeric acid, isovaleric acid, hexanoic acid and the like. Examples of the aryl aliphatic carboxylic acid include those having 8 to 9 carbon atoms such as phenylacetic acid, phenylpropionic acid and the like. Examples of the aromatic carboxylic acid include those having 7 to 8 carbon atoms such as benzoic acid and the like. These aromatic ring can be substituted by one or more substituents such as halogen atom (fluorine, chlorine, bromine or the like), lower alkoxy having 1 to 4 carbon atoms (e.g., methoxy, ethoxy or the like), trifluoromethyl or the like.

The amount of the acylating agent to be used is normally 1 to 10 mol, preferably 1 to 2 mol per 1 mol of the compound (I-1). Examples of the base include amines such as pyridine, methylamine and the like, carbonates and bicarbonates such as sodium carbonate, potassium carbonate, sodium bicarbonate, potassium bicarbonate and the like. The base to be used is normally equal or in

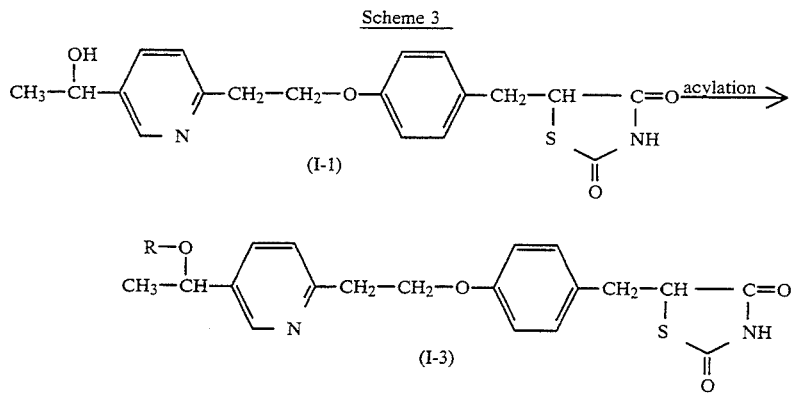

This acylation is normally carried out by reacting the compound (I-1) with an acylating agent in a suitable solvent in the presence of a base. Examples of the solvent include esters such as ethyl acetate and the like, aromatic hydrocarbons such as benzene, toluene, xylene and the like, ethers such as diethyl ether, diisopropyl ether, tetrahydrofuran, dioxane and the like, ketones such as acetone, methyl ethyl ketone and the like, chlorinated hydrocarbons such as dichloromethane, chloroform, carbon tetrachloride and the like, dimethylformamide and the like. Examples of the acylating agent include formic acid and acid anhydrides and acid halarge excess based on the acylating agent. When pyridine is used as the base, the pyridine in large excess can also be used as the solvent. The reaction is carried out at $-20°$ to $+40°$ C. The reaction time is normally 10 minutes to 24 hours.

(4) Production of the compound (I) wherein X is $-CH_2-$ and Q is $-CH_2COOH$

This compound (I-4) can be produced according to the Scheme 4.

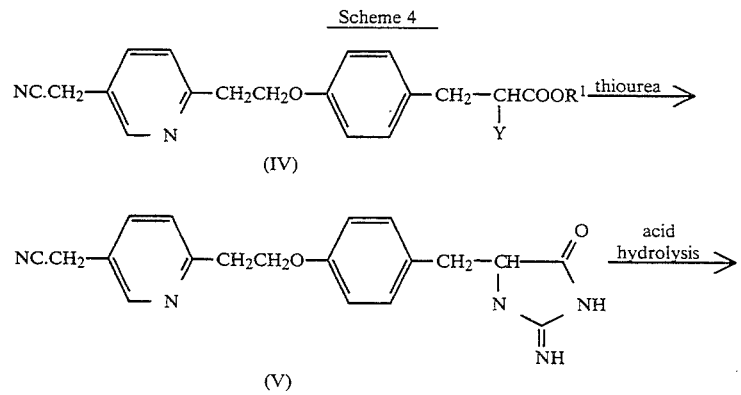

Scheme 4

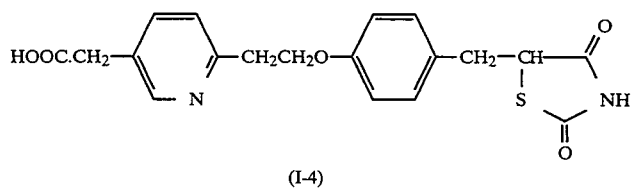

(I-4)

wherein Y is as defined above.

The reaction of the compound (IV) with thiourea can be carried out according to the same manner as that described with respect to the reaction of the compound (II) with thiourea to obtain the compound (V). The acid hydrolysis of the compound (V) can be carried out according to the same manner as that described with respect to the hydrolysis of the compound (III).

(5) Production of the compound (I) wherein X is

—CO— and Q is $CH_3CH_2$—

This compound (I-5) can be produced according to the Scheme 5.

Scheme 5

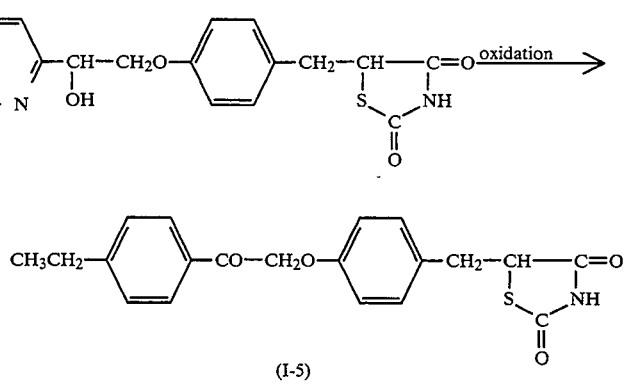

(I-5)

The oxidation can be carried out according to the same manner as that described with respect to the oxidation of the compound (I-1) to the compound (I-2).

The compound (I), its salt or stereoisomeric form thus obtained can be isolated and purified by known separation and purification techniques such as concentration, concentration under reduced pressure, crystallization, recrystallization, dissolution in a different solvent, chromatography or the like.

The starting material (II) can be produced according to the Scheme 6.

Scheme 6

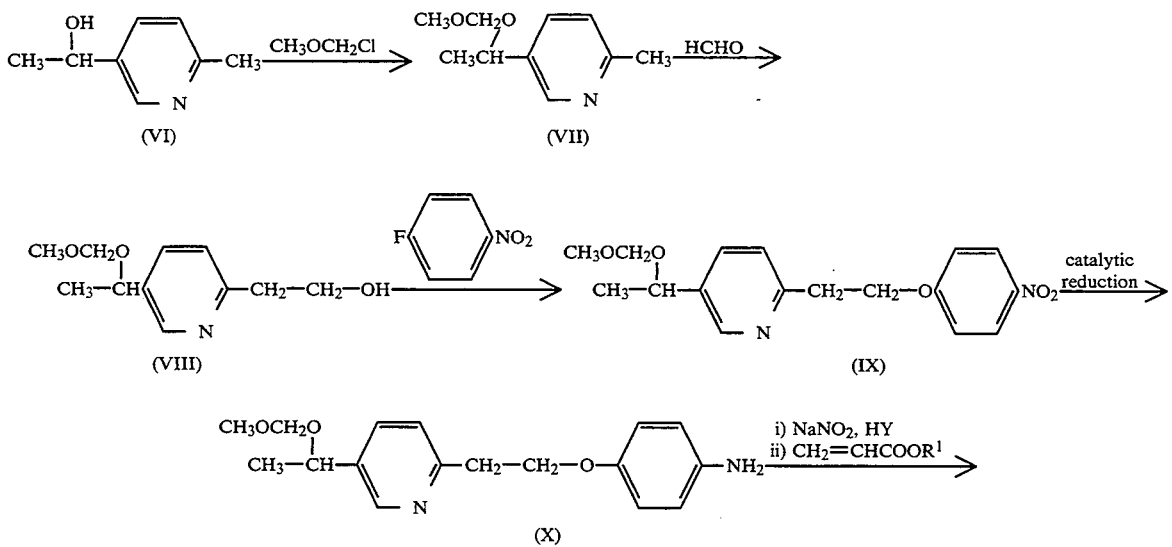

Scheme 6

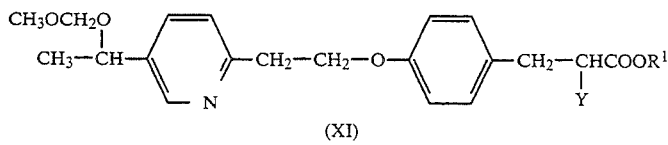

wherein Y is as defined above.

Conversion of the compound (VI) into the compound (VII) is carried out by reacting the compound (VI) with chloromethyl methyl ether in the presence of sodium hydride, sodium hydroxide, potassium hydroxide or the like.

The reaction can be carried out in a solvent such as dimethylformamide, dimethyl sulfoxide, tetrahydrofuran or the like at $-20°$ to $+60°$ C. Then, the compound (VII) is reacted with formalin at 100° to 180° C. to produce the compound (VIII). Conversion of the compound (VIII) into the compound (IX) is carried out by reacting the compound (VIII) with 4-fluoronitrobenzene in the presence of sodium hydride, sodium hydroxide, potassium hydroxide or the like.

The reaction can be carried out in a solvent such as dimethylformamide, dimethyl sulfoxide, tetrahydrofuran or the like at $-20°$ to $+60°$ C. Catalytic hydrogenation of the compound (IX) is carried out, for example, by using palladium on carbon as a catalyst according to a conventional manner to obtain the compound (X). Conversion of the compound (X) into the compound (XI) is carried out by subjecting the compound (X) to diazotization in the presence of a hydrogen halide followed by so-called Meerwein arylation wherein the diazo compound is reacted with acrylic acid or its esters in the presence of a copper catalyst (e.g., cuprous oxide, cupric oxide, cuprous chloride, cupric chloride, cuprous bromide, cupric bromide, etc.).

The compound (IV) can be produced according to the Scheme 7.

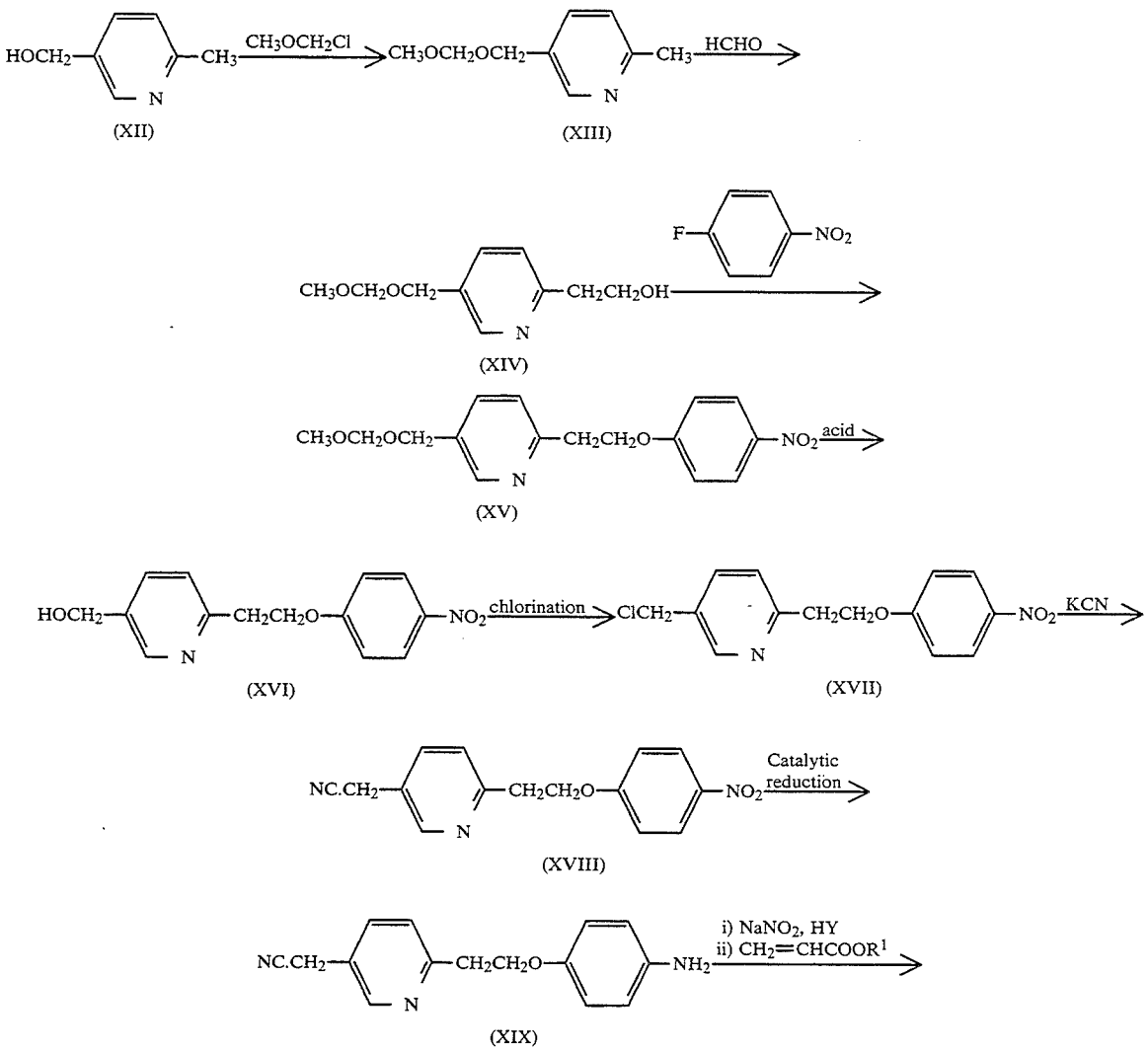

-continued

Scheme 7

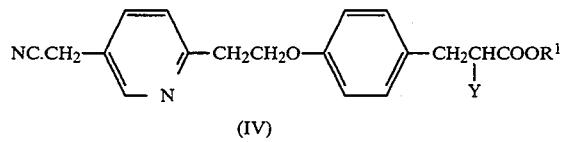

(IV)

In this process, the compound (XV) prepared according to the same manner as that described with respect to the production of compound (IX) is reacted with an acid to obtain the compound (XVI). This reaction can be carried out in the presence of an acid such as hydrochloric acid, sulfuric acid or the like in a solvent containing water at 0° to 100° C. The compound (XVI) is chlorinated with thionyl chloride to obtain the compound (XVII). The compound (XVII) is reacted with potassium cyanide (or sodium cyanide) in a solvent such as acetone, dioxane, N,N-dimethylformamide, dimethylsulfoxide or the like at 0° to 100° C. to obtain the compound (XVIII). The compound (XVIII) is subjected to catalytic reduction according to the same manner as that described with respect to the compound (IX) to obtain the compound (IV).

The starting material of the above Scheme 5 is known and disclosed in U.S. Pat. No. 4,582,839.

The following Experiment shows that the compound (I) of the present invention has excellent hypoglycemic and hypolipidemic activities.

Experiment

Hypoglycemic and hypolipidemic activities in mice

Test compounds were mixed with laboratory chow diet (CE-2, Clea Japan Inc., Tokyo, Japan) in a proportion of 0.005% by weight. The dietary admixture was given freely to KKA$^Y$-mice (male, 9 to 10 weeks old) for 4 days. During the period, water was given freely. Blood was collected from the orbitral venous plexus. The blood sugar level was determined according to glucose oxidase method. The plasma lipid level was enzymatically determined by using Kit Cleantech TG-S (Iatron, Tokyo, Japan). The results are shown in Table 1. Values represent % reduction from control groups.

TABLE 1

| Compound (Example No.) | Hypoglycemic activity (%) | Hypolipidemic activity (%) |
| --- | --- | --- |
| 1 | 46 | 5 |
| 2 | 56 | 43 |

As is clear from Table 1, the compound (I) of the present invention has excellent hypoglycemic and hypolipidemic activities, and is useful for a therapeutic agent for treating diabetes, hyperlipidemia and the like.

Further, the compound (I) of the present invention causes neither lactic acidosis nor serious hypoglycemia.

As described hereinabove, according to the present invention, there is provided novel thiazolidinedione derivatives or salts thereof which have excellent hypoglycemic and hypolipidemic activities without causing lactic acidosis and hypoglycemia.

The following Examples and Reference Examples further illustrates the present invention in detail but are not to be construed to limit the scope of the invention.

EXAMPLE 1

A mixture of methyl 2-bromo-3-[4-[2-[5-(1-methoxymethoxyethyl)-2-pyridyl]ethoxy]phenyl]propionate (27.0 g), thiourea (4.6 g), sodium acetate (4.9 g) and ethanol (250 ml) was heated under reflux for 4 hours. To the reaction mixture was added 2N hydrochloric acid (250 ml). The mixture was further heated under reflux for 20 hours and concentrated under reduced pressure. The residue was neutralized with saturated aqueous sodium bicarbonate solution and extracted with ethyl acetate. The ethyl acetate layer was washed with water, dried over anhydrous magnesium sulfate and concentrated under reduced pressure. The oily residue thus obtained was subjected to silica gel column chromatography. A fraction eluted with chloroform-methanol (40:1, v/v) gave 5-[4-[2-[5-(1-hydroxyethyl)-2-pyridyl]ethoxy]benzyl]-2,4-thiazolidinedione (14.8 g, yield: 66%). This crude compound was recrystallized from ethanol to obtain colorless prisms, m.p. 155°–156° C.

Elemental Analysis for $C_{19}H_{20}N_2O_4S \cdot \frac{1}{4}C_2H_5OH$,
Calcd.: C, 61.00; H, 5.64; N, 7.30
Found : C, 60.87; H, 5.70; N, 7.31

EXAMPLE 2

Acetic anhydride (25 ml) was added to a solution of 5-[4-[2-[5-(1-hydroxyethyl)-2-pyridyl]ethoxy]benzyl]-2,4-thiazolidinedione (8.7 g) in dimethyl sulfoxide (100 ml). The mixture was allowed to stand at room temperature for 4 days. The reaction mixture was poured into water and extracted with ethyl acetate. The ethyl acetate layer was washed with water, dried over anhydrous magnesium sulfate and concentrated under reduced pressure. The oily residue was subjected to silica gel column chromatography. A fraction eluted with chloroform-methanol (100:1, v/v) gave 5-[4-[2-(5-acetyl-2-pyridyl)ethoxy]benzyl]-2,4-thiazolidinedione. This compound was recrystallized from ethanol to obtain colorless prisms, m.p. 114°–115° C.

Elemental Analysis for $C_{19}H_{18}N_2O_4S \cdot \frac{1}{4}C_2H_5OH$,
Calcd.: C, 61.32; H, 5.15; N, 7.33
Found: C, 61.40; H, 5.08; N, 7.43

EXAMPLE 3

5-[4-[2-[5-(1-Hydroxyethyl)-2-pyridyl]ethoxy]benzyl]-2,4-thiazolidinedione (0.3 g) was dissolved in hydrogen chloride-ethanol (25%, 1 ml). The solution was stirred at room temperature for 30 minutes and precipitated crystals were filtered off. The crystals were recrystallized from ethanol to obtain 5-[4-[2-[5-(1-hydroxyethyl)-2-pyridyl]ethoxy]benzyl]-2,4-thiazolidinedione hydrochloride (0.21 g, yield: 62%) as colorless prisms, m.p. 212°–213° C.

Elemental Analysis for $C_{19}H_{20}N_2O_4S \cdot HCl \cdot \frac{1}{4}C_2H_5OH$,
Calcd.: C, 55.71; H, 5.39; N, 6.66
Found : C, 55.75; H, 5.36; N, 6.77

EXAMPLE 4

A mixture of 5-[4-[2-[5-(1-hydroxyethyl)-2-pyridyl]-benzyl]-2,4-thiazolidinedione.¼ ethanol (384 mg), acetic anhydride (0.5 ml) and pyridine (5 ml) was stirred at room temperature for 12 hours. After addition of water (5 ml), the mixture was concentrated under reduced pressure and the remaining crystals were filtered off. The crystals were recrystallized from ethyl acetate-hexane to obtain 5-[4-[2-[5-(1-acetoxyethyl)-2-pyridyl]ethoxy]benzyl]-2,4-thiazolidinedione (345 mg, yield: 83%) as colorless prisms, m.p. 143°–144° C.

Elemental Analysis for $C_{21}H_{22}N_2O_5S$,
Calcd.: C, 60.85; H, 5.35; N, 6.76
Found : C, 60.73; H, 5.45; N, 6.79

EXAMPLE 5

A mixture of 5-[4-[2-(5-cyanomethyl-2-pyridyl)ethoxy]benzyl]-2-imino-4-thiazolidinone (2.3 g) and 4N hydrochloric acid (100 ml) was heated under reflux for 24 hours and concentrated under reduced pressure. The residue was neutralized with saturated aqueous solution of sodium bicarbonate and acidified with addition of acetic acid. Crystals precipitated were filtered off and dissolved in ethyl acetate (200 ml)-methanol (200 ml). The resulting solution was washed with water and dried over magnesium sulfate and the solvent was distilled off to obtain 5-[4-[2-(5-carboxymethyl-2-pyridyl)ethoxy]benzyl]-2,4-thiazolidinedione (1.9 g, yield: 79%). This compound was recrystallized from ethanol to obtain colorless prisms, m.p. 144°–145° C.

Elemental Analysis for $C_{19}H_{18}N_2O_5S$,
Calcd.: C, 59.06, H, 4.70; N, 7.25
Found : C, 58.89; H, 4.69; N, 7.08

EXAMPLE 6

A mixture of 5-[4-[2-(5-ethyl-2-pyridyl)-2-hydroxyethoxy]benzyl]-2,4-thiazolidinedione. ½ $C_2H_5OH$ (396 mg), acetic anhydride (1.5 ml) and dimethylsulfoxide (4 ml) was stirred at room temperature for 5 hours and then poured into water. The mixture was extracted with ethyl acetate. The ethyl acetate layer was washed with water and dried over magnesium sulfate and the solvent was distilled off. The oily residue was subjected to silica gel chromatography. A fraction eluted with chloroform-methanol (100:1, v/v) gave 5-[4-[2-(5-ethyl-2-pyridyl)-2-oxoethoxy]benzyl]-2,4-thiazolidinedione (75 mg, yield: 20%). This was recrystallized from ethyl acetate-hexane to obtain colorless prisms, m.p. 148°–149° C.

Elemental Analysis for $C_{19}H_{18}N_2O_4S$,
Calcd.: C, 61.61; H, 4.90; N, 7.56
Found : C, 61.39; H, 4.91; N, 7.37

EXAMPLE 7

Preparation of tablets

Tablets are prepared according to the following formulation.

| | | |
|---|---|---|
| (1) 5-[4-[2-[5-(1-hydroxyethyl)-2-pyridyl]ethoxy]benzyl]-2,4-thiazolidinedione ¼ ethanol solvate | | 100 g |
| (2) Lactose | | 50 g |
| (3) Corn starch | | 15 g |
| (4) Calcium carboxymethylcellulose | | 44 g |
| (5) Magnesium stearate | | 1 g |
| | 1000 tablets | 210 g |

All the ingredients of (1), (2) and (3), and 30 g of the ingredient (4) were kneaded with water. The mixture was dried under vacuum and then granulated. The granules were mixed with 14 g of the ingredient (4) and 1 g of the ingredient (5). The resulting mixture was compressed into tablets by a tablet machine to produce 1000 tablets of 8 mm in diameter containing 100 mg of the ingredient (1) per tablet.

Reference Example 1

Sodium hydride in oil (60%, 7.0 g) was added with ice-cooling to a solution of 5-(1-hydroxyethyl)-2-methylpyridine (20.0 g) in N,N-dimethylformamide (120 ml). The mixture was stirred for 15 minutes. Then, chloromethyl methyl ether (14.1 g) was added dropwise at the same temperature. The reaction mixture was further stirred for 30 minutes with ice-cooling. The mixture was poured into water and extracted with ethyl acetate. The ethyl acetate layer was washed with water, dried over anhydrous magnesium sulfate and subjected to distillation under reduced pressure to obtain 5-(1-methoxymethoxyethyl)-2-methylpyridine (21.5 g, yield: 81%), b.p. 78°–80° C./0.8 mmHg.

Reference Example 2

The mixture of 5-(1-methoxymethoxyethyl)-2-methylpyridine (21.0 g) and formalin (37% aq. HCHO, 14.1 g) was heated at 150° to 160° C. for 8 hours in a sealed tube. The reaction mixture was concentrated under reduced pressure and then the residue was subjected to silica gel column chromatography. A fraction eluted with chloroform-methanol (25:1, v/v) gave 2-[5-(1-methoxymethoxyethyl)-2-pyridyl]ethanol (7.8 g, yield: 32%) as oil.

NMR (δppm in $CDCl_3$): 1.49 (3H, d, J=7 Hz), 3.01 (2H, t, J=6 Hz), 3.36 (3H, s), 4.03 (2H, t, J=6 Hz), 4.53 (1H, d, J=7 Hz), 4.61 (1H, d, J=7 Hz), 4.77 (1H, d, J=7 Hz), 7.15 (1H, d, J=8 Hz), 7.62 (1H, dd, J=8 and 2 Hz), 8.46 (1H, d, J=2 Hz).

Reference Example 3

Sodium hydride in oil (60%, 1.6 g) was added in small portions with ice-cooling to a solution of 2-[5-(1-methoxymethoxyethyl)-2-pyridyl]ethanol (7.5 g) and 4-fluoronitrobenzene (5.0 g) in N,N-dimethylformamide (50 ml). The reaction mixture was stirred with ice-cooling for additional 1 hour, poured into water and extracted with ethyl acetate. The ethyl acetate layer was washed with water, dried over anhydrous magnesium sulfate and concentrated under reduced pressure. The oily residue was subjected to silica gel column chromatography. A fraction eluted with chloroform-methanol (40:1, v/v) gave 5-(1-methoxymethoxyethyl)-2-[2-(4-nitrophenoxy)ethyl]pyridine (8.4 g, yield: 71%) as oil.

NMR (δppm in $CDCl_3$): 1.49 (3H, d, J=7 Hz), 3.30 (2H, t, J=6 Hz), 3.36 (3H, s), 4.48 (2H, t, J=6 Hz), 4.52 (1H, d, J=7 Hz), 4.62 (1H, d, J=7 Hz), 4.79 (1H, d, J=7 Hz), 6.97 (2H, d, J=9 Hz), 7.25 (1H, d, J=8 Hz), 7.64 (1H, dd, J=8 and 2 Hz), 8.18 (2H, d, J=9 Hz), 8.53 (1H, d, J=2 Hz).

Reference Example 4

A mixture of 5-(1-methoxymethoxyethyl)-2-[2-(4-nitrophenoxy)ethyl]pyridine (8.2 g), 5% palladium-carbon (50% wet, 0.8 g) and ethyl acetate (100 ml) was subjected to catalytic reduction at room temperature and at the pressure of 1 atm. The catalyst was filtered off and the filtrate was concentrated under reduced pressure. The oily residue was dissolved in acetone (80 ml)-hydrobromic acid (47%, 16.9 g). A solution of sodium nitrite (1.9 g) in water (5 ml) was added dropwise at 0° to 5° C. The reaction mixture was stirred at 5° C. for additional 20 minutes. Then, methyl acrylate (12.7 g) was added thereto and the resulting mixture was warmed to 37° C. While this mixture was stirred vigorously, cuprous oxide (0.3 g) was added in small portions to the mixture. After the evolution of nitrogen gas had ceased, the reaction mixture was concentrated under reduced pressure. The residue was made basic with conc. $NH_4OH$ and extracted with ethyl acetate. The ethyl acetate layer was washed with water, dried over anhydrous magnesium sulfate and concentrated under reduced pressure. The oily residue was subjected to silica gel column chromatography. A fraction eluted with ether-hexane-triethylamine (25:25:1, v/v) gave methyl 2-bromo-3-[4-[2-[5-(1-methoxymethoxyethyl)-2-pyridyl]ethoxy]phenyl]propionate (5.6 g, yield: 50 %) as oil.

NMR ($\delta$ppm in $CDCl_3$): 1.48 (3H, d, J=7 Hz), 3.1–3.4 (2H, m), 3.24 (2H, t, J=6 Hz), 3.36 (3H, s), 3.71 (3H, s), 4.33 (2H, t, J=6 Hz), 4.53 (1H, d, J=7 Hz), 4.61 (1H, d, J=7 Hz), 4.5–4.7 (1H, m), 4.77 (1H, q, J=6 Hz), 6.83 (2H, d, J=9 Hz), 7.09 (2H, d, J=9 Hz), 7,245 (1H, d, J=8 Hz), 7.61 (1H, dd, J=8 and 2 Hz), 8.50 (1H, d, J=2 Hz).

Reference Example 5

A solution of methyl 6-methylnicotinate (45.4 g) in tetrahydrofuran (50 ml) was added dropwise to a suspension of lithium aluminium hydride ($LiAlH_4$, 5.7 g) in tetrahydrofuran (250 ml) at room temperature. The mixture was stirred at room temperature for additional 1 hour and water (30 ml) was added dropwise with ice-cooling. Insoluble materials were filtered off and the filtrate was concentrated. The residue was distilled under reduced pressure to obtain 6-methyl-3-pyridylmethanol (31 g, yield: 84%), b.p. 98°–100° C./0.5 mmHg.

Reference Example 6

6-Methyl-3-pyridylmethaol (30.8 g) was dissolved in tetrahydrofuran (200 ml) and sodium hydride in oil (60%, 11 g) was added thereto. The mixture was stirred with ice-cooling for 30 minutes. Then, chloromethyl methyl ether (22.1 g) was added dropwise with ice-cooling and the mixture was stirred for additional 1 hour. The mixture was poured into water and extracted with ethyl acetate. The ethyl acetate layer was washed with water and dried over magnesium sulfate and the solvent was distilled off under reduced pressure to obtain 5-methoxymethoxymethyl-2-methylpyridine (31 g, yield: 74%), b.p. 85°–87° C./0.5 mmHg.

Reference Example 7

A mixture of 5-methoxymethoxymethyl-2-methylpyridine (30.5 g) and formalin (37% aq., HCHO, 22.2 g) was heated in a sealed tube at 150° to 160° C. for 8 hours. The reaction mixture was concentrated under reduced pressure and the oily residue was subjected to silica gel column chromatography. A fraction eluted with chloroform-methanol (20:1, v/v) gave 2-(5-methoxymethoxymethyl-2-pyridyl)ethanol (11.8 g, yield: 33%) as oil.

NMR ($\delta$ ppm in $CDCl_3$): 3.02 (2H, t, J=6 Hz), 3.41 (3H, s), 4.02 (2H, t, J=6 Hz), 4.59 (2H, s), 4.71 (2H, s), 7.16 (1H, d, J=8 Hz), 7.64 (1H, dd, J=8 and 2 Hz), 8.48 (1H, d, J=2 Hz).

Reference Example 8

To a solution of 2-(5-methoxymethoxymethyl-2-pyridyl)ethanol (11.6 g) and 4-fluoronitrobenzene (8.5 g) in N,N-dimethylformamide (100 ml) was added by portions sodium hydride in oil (60%, 2.8 g) with ice-cooling. The reaction mixture was stirred with ice-cooling for additional 1 hour, poured into water and then extracted with ethyl acetate. The ethyl acetate layer was washed with water, dried over magnesium sulfate and concentrated under reduced pressure. The oily residue was subjected to silica gel column chromatography. A fraction eluted with chloroform-methanol (40:1, v/v) gave 5-methoxymethoxymethyl-2-[2-(4-nitrophenoxy)ethyl]pyridine (14.7 g, yield: 79%) as oil.

NMR ($\delta$ ppm in $CDCl_3$): 3.30 (2H, t, J=6 Hz), 3.41 (3H, s), 4.47 (2H, t, J=6 Hz), 4.60 (2H, s), 4.71 (2H, s), 6.94 (2H, d, J=9 Hz), 7.26 (1H, d, J=8 Hz), 7.66 (1H, dd, J=8 and 2 Hz), 8.17 (2H, d, J=9 Hz), 8.54 (1H, d, J=2 Hz).

Reference Example 9

A mixture of 5-methoxymethoxymethyl-2-[2-(4-nitrophenoxy)ethyl]pyridine (14.5 g), 2N hydrochloric acid (50 ml) and methanol (50 ml) was stirred under reflux for 2 hours. The reaction mixture was concentrated and the residue was neutralized with saturated aqueous solution of sodium bicarbonate and extracted with ethyl acetate. The ethyl acetate layer was washed with water, dried over magnesium sulfate and concentrated under reduced pressure to obtain 5-hydroxymethyl-2-[2-(4-nitrophenoxy)ethyl]pyridine (9.7 g, yield: 88%). This compound was recrystallized from ethyl acetate to obtain colorless prisms, m.p. 144°–145° C.

Elemental Analysis for $C_{14}H_{14}N_2O_4$,
Calcd.: C, 61.31; H, 5.14; N, 10.21
Found : C, 61.01; H, 5.14; N, 10.13.

Reference Example 10

To a solution of 5-hydroxymethyl-2-[2-(4-nitrophenoxy)ethyl]pyridine (9.4 g) in chloroform (100 ml) was added thionyl chloride (7.0 g) and the mixture was stirred under reflux for 30 minutes. After cooling, the reaction mixture was washed with saturated aqueous solution of sodium bicarbonate and then water, dried over magnesium sulfate and concentrated under reduced pressure to obtain 5-chloromethyl-2-[2-(4-nitrophenoxy)ethyl]pyridine (9.7 g, yield: 85%). The compound was recrystallized from ethyl acetate-hexane to obtain colorless needles, m.p. 77°–78° C.

Elemental Analysis for $C_{14}H_{13}N_2O_3Cl$,
Calcd.: C, 57.44; H, 4.48; N, 9.57
Found: C, 57.07, H, 4.42; N, 9.46.

Reference Example 11

A mixture of 5-chloromethyl-2-[2-(4-nitrophenoxy)ethyl]pyridine (9.5 g), potassium cyanide (3.2 g) and N,N-dimethylformamide (100 ml) was stirred at 60° C. for 2 hours. The reaction mixture was poured into water and extracted with ethyl acetate. The ethyl acetate layer was washed with water, dried over magnesium sulfate and concentrated under reduced pressure to obtain 5-cyanomethyl-2-[2-(4-nitrophenoxy)ethyl]pyridine (9.0 g, yield: 98%). This compound was recrystallized from ethyl acetate-hexane to obtain colorless prisms, m.p. 94°–95° C.

Elemental Analysis for $C_{15}H_{13}N_3O_3$,
Calcd.: C, 63.60; H, 4.63; N, 14.83
Found: C, 63.19; H, 4.63; N, 14.41.

Reference Example 12

A mixture of 5-cyanomethyl-2-[2-(4-nitrophenoxy)ethyl]pyridine (8.8 g), 5% palladium-carbon (50% wet, 1.0 g) and ethyl acetate (100 ml) was subjected to catalytic reduction at room temperature and at the pressure of 1 atm. The catalyst was filtered off and the filtrate was concentrated under reduced pressure. The oily residue was dissolved in acetone (80 ml)-hydrobromic acid (47%, 21.4 g). To the solution was added dropwise a solution of sodium nitrite (2.4 g) in water (5 ml) at 0° to 5° C. The reaction mixture was stirred at 5° C. for additional 20 minutes and methyl acrylate (16.1 g) was added thereto. The mixture was warmed to 37° C. and cuprous oxide (0.3 g) was added in small portions, while the mixture was vigorously stirred. After the evolution of nitrogen gas had ceased, the reaction mixture was concentrated under reduced pressure and the residue was made basic with conc. $NH_4OH$ and extracted with ethyl acetate. The ethyl acetate layer was washed with water, dried over magnesium sulfate, and concentrated under reduced pressure. The oily residue was subjected to silica gel column chromatography. A fraction eluted with ether-hexane-triethylamine (25:25:1, v/v) gave methyl 2-bromo-3-[4-[2-(5-cyanomethyl-2-pyridyl)ethoxy]-phenyl]propionate (7.3 g, yield: 58%) as oil.

NMR ($\delta$ ppm, $CDCl_3$): 3.1–3.4 (2H, m), 3.26 (2H, t, J=6 Hz), 3.71 (2H, s), 3.74 (3H, s), 4.3–4.4 (1H, m), 4.33 (2H, t, J=6 Hz), 6.76 (2H, d, J=9 Hz), 7.2–7.4 (3H, m), 7.65 (1H, dd, J=8 and 2 Hz), 8.50 (1H, d, J=2 Hz).

Reference Example 13

A mixture of methyl 2-bromo-3-[4-[2-(5-cyanomethyl-2-pyridyl)ethoxy]phenyl]propionate (7.2 g), thiourea (1.2 g), sodium acetate (1.3 g) and ethanol (80 ml) was heated under reflux for 5 hours and concentrated under reduced pressure. To the residue was added saturated aqueous sodium bicarbonate solution (100 ml)-ether (50 ml) and the mixture was stirred for 15 minutes. The precipitated crystals were filtered off to obtain 5-[4-[2-(5-cyanomethyl-2-pyridyl)ethoxy]benzyl]-2-imino-4-thiazolidinone (2.5 g, yield: 38%). This compound was recrystallized from chloroform-methanol to obtain colorless prisms, m.p. 211°–212° C.

Elemental Analysis for $C_{19}H_{18}N_4O_2S$,
Calcd.: C, 62.28; H, 4.95; N, 15.29
Found : C, 62.21; H, 4.89; N, 15.15.

What is claimed is:

1. A thiazolidinedione compound of the formula (I):

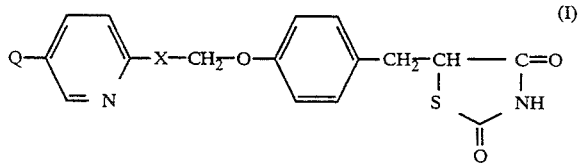

(I)

wherein X is —$CH_2$— or —CO—;
wherein Q is $CH_3CO$—, $CH_3CH(OR)$—, —$CH_2COOH$, or $CH_3CH_2$—;
wherein R is a hydrogen atom or a formyl or alkylcarbonyl group having two to six carbon atoms; with the provisio that Q is $CH_3CO$—, $CH_3CH(OR)$—, or —$CH_2COOH$ only when X is —$CH_2$— and Q is $CH_3CH_2$— only when X is —CO—;
or a pharmaceutically acceptable salt thereof, or a pure stereoisomeric form thereof.

2. A thiazolidinedione compound according to claim 1, wherein X is —$CH_2$— or —CO—, Q is $CH_3CO$— or $CH_3CH(OR)$—, when X is —$CH_2$—, wherein R is an acyl group, or Q is $CH_3CH_2$—, when X is —CO—.

3. A thiazolidinedione compound according to claim 1, wherein X is —$CH_2$— and Q is $CH_3CH(OH)$— or —$CH_2COOH$.

4. The thiazolidinedione compound according to claim 1 which is 5-[4-[2-(5-acetyl-2-pyridyl)ethoxy]benzyl]-2,4-thiazolidinedione or its salt.

5. The thiazolidinedione compound according to claim 1 which is 5-[4-[2-[5-(1-hydroxyethyl)-2-pyridyl]ethoxy]benzyl]-2,4-thiazolidinedione or its salt.

6. The thiazolidinedione compound according to claim 1 which is 5-[4-[2-[5-(1-acetoxyethyl)-2-pyridyl]ethoxy]benzyl]-2,4-thiazolidinedione or its salt.

7. The thiazolidinedione compound according to claim 1 which is 5-[4-[2-[5-(1-propionyloxyethyl)-2-pyridyl]ethoxy]benzyl]-2,4-thiazolidinedione or its salt.

8. The thiazolidinedione compound according to claim 1 which is 5-[4-[2-[5-(1-butyryloxyethyl)-2-pyridyl]ethoxy]benzyl]-2,4-thiazolidinedione or its salt.

9. The thiazolidinedione compound according to claim 1 which is 5-[4-[2-[5-(1-isobutyryloxyethyl)-2-pyridyl]ethoxy]benzyl]-2,4-thiazolidinedione or its salt.

10. The thiazolidinedione compound according to claim 1 which is 5-[4-[2-[5-(1-valeryloxyethyl)-2-pyridyl]ethoxy]benzyl]-2,4-thiazolidinedione or its salt.

11. The thiazolidinedione compound according to claim 1 which is 5-[4-[2-[5-(1-isovaleryloxyethyl)-2-pyridyl]ethoxy]benzyl]-2,4-thiazolidinedione or its salt.

12. The thiazolidinedione compound according to claim 1 which is 5-[4-[2-[5-(1-pivaloyloxyethyl)-2-pyridyl]ethoxy]benzyl]-2,4-thiazolidinedione or its salt.

13. The thiazolidinedione compound according to claim 1 Which is 5-[4-[2-(5-carboxymethyl-2-pyridyl)ethoxy] benzyl]-2,4-thiazolidinedione or its salt.

14. The thiazolidinedione compound according to claim 1 which is 5-[4-[2-(5-ethyl-2-pyridyl)-2-oxoethoxy]benzyl]-2,4-thiazolidinedione or its salt.

15. The thiazolidinedione compound which is according to claim 1 which is 5-[4-[2-[5-(1-benzoyloxyethyl)-2-pyridyl]ethoxy]benzyl]-2,4-thiazolidinedione or its salt.

16. A pharmaceutical composition for treating diabetes comprising the thiazolidinedione derivative according to claim 1, and a pharmacologically acceptable carrier, excipient or diluent.

17. A pharmaceutical composition for treating diabetes comprising the thiazolidinedione derivative according to claim 2, and a pharmacologically acceptable carrier, excipient or diluent.

18. A pharmaceutical composition for treating diabetes comprising the thiazolidinedione derivative according to claim 3, and a pharmacologically acceptable carrier, excipient or diluent.

19. A method for treating diabetes which comprising administering an effective amount of the thiazolidinedione derivative according to claim 1, optionally together with a pharmacologically acceptable carrier, excipient or diluent to a patient requiring such a treatment.

20. A method for treating diabetes which comprising administering an effective amount of the thiazolidinedione derivatives according to claim 2, optionally together with a pharmacologically acceptable carrier, excipient or diluent to a patient requiring such a treatment.

21. A method for treating diabetes which comprising administering an effective amount of the thiazolidinedione derivatives according to claim 3, optionally together with a pharmacologically acceptable carrier, excipient or diluent to a patient requiring such a treatment.

* * * * *